United States Patent
Hardy

Patent Number: 6,022,556
Date of Patent: Feb. 8, 2000

[54] SWELLABLE WOUND DRESSING MATERIALS

[75] Inventor: Craig J. Hardy, Utley, United Kingdom

[73] Assignee: Johnson & Johnson Medical, Inc., Arlington, Tex.

[21] Appl. No.: 08/201,522

[22] Filed: Feb. 25, 1994

[30] Foreign Application Priority Data

Mar. 3, 1993 [GB] United Kingdom ............ 9304310

[51] Int. Cl.[7] .................................................. A61K 9/70
[52] U.S. Cl. .................................. 424/443; 424/404
[58] Field of Search ........................... 424/443, 404

[56] References Cited

U.S. PATENT DOCUMENTS

| | | | |
|---|---|---|---|
| 4,364,929 | 12/1982 | Sasmor et al. | 424/80 |
| 4,393,048 | 7/1983 | Mason, Jr. et al. | 424/132 |
| 4,793,337 | 12/1988 | Freeman et al. | 128/156 |

FOREIGN PATENT DOCUMENTS

| | | | |
|---|---|---|---|
| 0 095 892 | 12/1983 | European Pat. Off. | A61L 15/01 |
| 0 099 758 | 2/1984 | European Pat. Off. | A61F 13/00 |
| 0 227 955 | 7/1987 | European Pat. Off. | A61L 15/01 |
| 0 344 913 | 12/1989 | European Pat. Off. | A61L 15/01 |
| 0 439 339 A3 | 7/1991 | European Pat. Off. | D01F 9/04 |
| 0 459 378 A1 | 12/1991 | European Pat. Off. | A61L 15/16 |
| 0 532 275 A1 | 3/1993 | European Pat. Off. | A61L 15/28 |
| 0 568 368 A1 | 11/1993 | European Pat. Off. | A61L 25/00 |
| 906 911 | 9/1962 | United Kingdom . | |
| 1 379 158 | 2/1975 | United Kingdom | A61F 13/02 |
| WO 90/01954 | 3/1990 | WIPO | C08B 37/04 |

*Primary Examiner*—Thurman K. Page
*Attorney, Agent, or Firm*—Andrew C. Farmer

[57] ABSTRACT

The invention provides water swellable wound dressing materials comprising from 5% to 50% of an alginate ester of a $C_1$–$C_6$ polyhydric alcohol; from 50% to 95% of a humectant consisting of one or more $C_1$–$C_6$ monohydric or polyhydric alcohols; and from 0% to 30% of water, the percentages being calculated by weight based on the weight of the material when anhydrous. The preferred alginate ester is propylene glycol alginate (PGA). The materials swell but do not dissolve in cold or warm water. Insolubility is achieved by the addition of polyvaent cations such as calcium ions, or by covalent cross-linking of the pga, or by adding from 10 to 35% by weight of water-swellable polysaccharide such as gelatin, or by adding from 5% to 20% by weight of a cationic polymer such as chitosan.

19 Claims, No Drawings

SWELLABLE WOUND DRESSING MATERIALS

The present invention relates to water-swellable materials suitable for application to the surface of a wound as or in a wound dressing.

The use of biopolymers as the wound contacting layer of wound dressings is well known in the art. Biopolymers may be made absorbent, biocompatible and resorbable, thereby assisting wound healing. In addition, several biopolymers such as collagen, chitin, chitosan and alginates have been shown actively to assist wound healing by chemotaxis. Some biopolymers also exhibit a haemostatic effect.

Among the preferred biopolymers for wound healing applications are the alginates. This is on account of the abundance of alginates, their well-understood physicochemical properties and their proven chemotactic effect on wound healing. The alginates may be applied to the wound in a water-soluble form, for example by dusting sodium alginate powder onto the wound. Alternatively, the alginate may be applied as insoluble calcium alginate, or as an insoluble and water-swellable mixture of sodium alginate and calcium alainate. The soluble or insoluble alginate may be in the form of fibres, a fleece, a gauze or a film. It may be attached to other elements of a wound dressing such as an absorbent layer, a semipermeable or impermeable backing layer, and/or an adhesive-coated layer. Typical such alginate fleeces and wound dressings incorporating them are disclosed, for example, in GB-A-1379158, GB-A-906911, US-A-4793337, WO 90/01954, US-A-4393048, EP-A-0227955, EP-A-0099758, EP-A-0344913 and EP-A-0459378.

For many applications a continuous film of alginate is desirable as the wound contacting layer. Such a film presents a uniform contacting surface to the wound and helps to exclude bacteria from the wound. Continuous films are also easier to remove without disrupting the wound bed. Alternatively, the film may be perforated or reticulated to allow passage through the film of heavy flows of exudate from the wound while remaining easily removable.

In order to be useful, the alginate film should preferably be strong, elastic, highly conformable, inexpensive, absorbent and sterilizable by gamma irradiation. Preferably, the alginate film should contain a high proportion of humectant such as glycerol so as to maintain a moist wound surface.

Hitherto, no alginate-containing film has provided the optimum combination of properties for use as a wound dressing. For example, anhydrous films of calcium and/or sodium alginate have been suggested for this application. However, the anhydrous films may incorporate only up to about 10% by weight of humectant, which is insufficient for effective moisturising of the wound surface. Moreover, the high alginate content of the anhydrous films makes then relatively expensive. The amount of humectant incorporated in the films may be increased by incorporating water as well, and this also reduces the cost of the film. However, incorporation of water weakens the films. Films containing water present storage problems because they dry out in air. Films containing substantial amounts of water cannot be sterilized by gamma-irradiation.

EP-A-0459378 (FIDIA S.p.A) discloses films containing between 1% and 7.5% by weight of one or more alkali metal alginates such as sodium alginate, from 0.1% to 5% of an alkali earth alginate such as calcium alginate, from 0.1% to 10% of a polyhydric alcohol and from 0.05% to 10% of a hydrophilic polymer such as hyaluronic acid, the balance of the composition being mainly water. The film is made by extruding a solution containing sodium alginate into a calcium chloride bath, where insoluble calcium alginate is formed. The resulting film cannot be sterilised by gamma-irradiation and must be stored under a glycerol/water solution to prevent it from drying out.

EP-A-0095892 (Nippon Oil Co. Ltd.) discloses perforated wound-covering films that comprise: 1.5–8% by weight of a polyvinyl alcohol (PVA), from 10–85% by weight of a polyhydric alcohol humectant and from 0.2–15% by weight of a water-soluble macromolecular substance other than PVA. The water-soluble macromolecular substance is typically a biopolymer or derivative thereof, or a synthetic polymer, provided that it forms a viscous aqueous solution. Preferred macromolecular substances are pullulan, xanthan gum, tragacanth gum, carboxymethylcellulose, polyacrylic acid, i-carrageenan, λ-carrageenan or propylene glycol alginate (PGA). These wound covering films are inexpensive, moisturising, strong, anhydrous and swellable but not soluble in cold or warm water. The main drawback of these films is that the inclusion of PVA even at low concentrations such as 1.5% results in a film that is stiff and rubbery and insufficiently conformable to make a satisfactory wound dressing. The film that contains both PGA and PVA can provide some of the advantageous wound healing properties of the alginate, but the presence of PVA and the rubbery texture of the film mean that the rate of release of PGA into the wound is very slow.

Accordingly, it is an object of the present invention to provide wound dressing materials that are especially suitable for casting into highly conformable wound covering films, and that provide for rapid release of alginate into the wound bed.

The present invention provides a water swellable wound dressing material comprising, by weight based on the weight of the material when anhydrous: from 5% to 50% of an alginate ester of a $C_1$–$C_6$ polyhydric alcohol; from 50% to 95% of a humectant consisting of one or more $C_1$–$C_6$ monohydric or polyhydric alcohols, and from 0% to 30% of water, provided that the wound dressing material comprises less than 1.5% by weight of polyvinyl alcohol.

The term "water swellable" means that the wound dressing swells, but does not dissolve, in water at temperatures below 40° C. The wound dressing material is preferably substantially free of polyvinyl alcohol.

The preferred alginate ester is propylene glycol alginate (PGA). PGA is manufactured by reacting an alginate and propylene oxide at high temperatures. It is available, for example, from Protan Ltd., under the Registered Trade Mark PROTANAL. The viscosity and degree of esterification of the alginate ester are not critical to the materials of the present invention, but preferably the degree of esterification is between 35% and 95%. That is to say, between 35% and 95% of the carboxylate groups of the alginate are esterified with the one or more $C_1$–$C_6$ polyhydric alcohols. The remaining carboxylate groups may be sodium carboxylate groups. Preferably, at least some of the remaining carboxylate groups are cross-linked to other alginate molecules, as described below.

The esterification of the alginate with a polyhydric alcohol greatly increases the affinity of the alginate for humectant consisting of one or more $C_1$–$C_6$ monohydric or polyhydric alcohols. Larger amounts of such humectant can be incorporated into wound dressing materials based on the alginate esters than can be incorporated into anhydrous sodium or calcium alginate materials. Preferably the materials according to the present invention comprise from 65% to 90% by weight of the humectant. The preferred humectants are the polyhydric alcohols. Preferably, the humectant comprises propylene glycol or glycerol. Other preferred humectants are sorbitol and mannitol.

The high humectant content of the materials according to the present invention makes them especially suitable for use as or in moisturising wound dressings. Furthermore, the material containing a high proportion of humectant are relatively inexpensive because the humectant is much less costly than alginate. The use of at least 5% by weight of the alginate ester allows surprisingly strong films to be 5 made without the need to add any reinforcing polymer such as PVA. Preferably the materials according to the present invention contain at least 10% by weight, more preferably more than 15% but less than 25% by weight of the alginate ester.

The affinity of the alginate ester for the humectant means that the above high humectant content can be achieved without the need for a high water content in the wound dressing material. Preferably, the materials according to the present invention contain from 5% to 15% by weight of water and more preferably they contain less than 5% by weight of water. The low water content makes the materials sterilizable by gamma-irradiation and also prevents the materials from drying out by evaporation when they are stored in air. Because of this variability in the water content of the films all of the weight percentages given for the components in the materials according to the present invention are based on the weight of the material when anhydrous.

The alginate esters normally need to be treated chemically or combined with other polymers in order to obtain a water swellable but insoluble material. The simplest method of obtaining an insoluble material is by introducing polyvalent cations such as calcium or zinc cations into the material. The polyvalent cations bond to two or more free carboxylate groups (i.e. carboxylate groups that are not esterified) on neighbouring alginate ester molecules, thereby effectively cross-linking the alginate chains and rendering the alginate insoluble. Alternatively, or additionally, effective cross-linking may be achieved by means of covalent cross-linking using chemical cross-linking agents such as epichlorohydrin, glutaraldehyde, formaldehyde δ-glucolactone or the like. Still more effective cross-linking may be achieved by including from 5% to 20% by weight of non-esterified alginate such as sodium alginate or alginic acid in the film. The increased strength of cross-linking in this case is presumably due to the larger number of free carboxylate groups available for cross-linking.

Another way to render the alginate ester both insoluble and water swellable is to include between 5% and 35% by weight of a cationic polymer in the material. The preferred cationic polymer is chitosan, such as the chitosan sold by Protan Biopolymers Ltd. under the Trade Mark SEA CURE.

Still another way to obtain a water swellable material is by including between 10% and 35% by weight of a water swellable biopolymer such as gelatin or a water swellable polysaccharide. Preferred water swellable polysaccharides are gellan gum and agar. The added water swellable biopolymer may in itself be wound-friendly and resorbable.

The materials according to the present invention optionally contain up to 5% by weight of dissolved salts. Preferably the dissolved salt content is 2% by weight or less of the composition. The dissolved salts preferably contain sodium chloride and may further comprise other salts in physiologically acceptable concentrations.

The materials according to the present invention preferably also comprise up to 2% by weight of a microbicide such as chlorhexidine or an antibiotic to provide protection against wound infection.

The materials according to the present invention preferably also comprise up to 25% by weight of one or more substances that are pharmacologically active to promote wound healing. These substances may comprise molecules such as cytokines and/or biopolymers such as collagen or chitin that have been shown to be effective at promoting wound healing.

The wound dressing materials according to the present invention may be prepared in any convenient physical form, such as a continuous or perforated film, a web, a foam or a fleece of woven or nonwoven fibres. Preferably the material is prepared as a continuous or perforated film.

The wound dressing materials according to the present invention are generally made by mixing the constituents with a small excess of water (normally less than 50% by weight), forming the resulting gel into the desired shape and evaporating the water at 50–100° C. Where there is a cross-linking agent -his may be present in the aqueous gel or added in post-treatment step, e.g. by extruding the gel into a bath containing the cross-linking agent.

Specific embodiments of the wound dressing materials according to the present invention will now be described further, by way of example.

EXAMPLE 1

A water swellable wound dressing film is prepared from the following constituents (percentages are by weight):

| | |
|---|---|
| 10% | Propylene Glycol Alginate (PGA) |
| 10% | Gelatin |
| 25% | Propylene Glycol |
| 25% | Glycerol |
| 0.9% | Sodium Chloride |
| 29.1% | Water |

The PGA is PROTANAL Ester PVH-A, available from Protan Ltd. It is characterised by a degree of esterification of 55%–65% and a viscosity (1% aqueous solution) of 1400±200 mPaS. The gelatin is calf skin gelatin (225 Bloom) available from Aldrich Chemical Company.

The wound dressing film is prepared as follows. The components are mixed thoroughly to form an aqueous gel, which is spread using a knife over a roll coater. The film is then dried for 1 hour at 80° C.

During the drying step the gelatin melts and then sets again, resulting in a uniform wound dressing film that is strong, moisturising and biocompatible. Also during the drying step essentially all of the water is evaporated from the gel. On standing in air, the resulting film takes up moisture until it reaches an equilibrium water content of 5–10%, depending on the ambient humidity.

EXAMPLE 2

A water swellable wound dressing film comprising crosslinked alginate ester is prepared from the following constituents (percentages are by weight):

| | | |
|---|---|---|
| A | 4% | Propylene Glycol Alginate (PGA) |
| B | 10% | Propylene Glycol |
| C | 10% | Glycerol |

-continued

| | | |
|---|---|---|
| D | 2% | Dicalcium Phosphate |
| E | 2% | δ-Glucolactone |
| F | 72% | Water |

The PGA is the same as that used in Example 1.

The wound dressing film is prepared as follows. The components, A,B, C and D are mixed thoroughly to form a first precursor mixture. Components E and F are mixed to form a second precursor mixture.

The first and second precursor mixtures are then mixed together to form an aqueous gel, which is spread using a knife over a roll coater to produce a film. The aqueous gel sets due to covalent cross-linking by the δ-glucolactone within 60 minutes at ambient temperature. The film is then dried in air at 80° C. for 1 hour.

EXAMPLE 3

A water swellable wound dressing film comprising alginate ester cross linked with unesterified alginate is prepared from the following constituents (percentages are by weight):

| | | |
|---|---|---|
| A | 2% | Propylene Glycol Alginate (PGA) |
| B | 2% | Sodium Alginate |
| C | 10% | Propylene Glycol |
| D | 10% | Glycerol |
| E | 2% | Dicalcium Phosphate |
| F | 2% | δ-Glucolactone |
| G | 72% | Water |

The PGA is the same as that used in Examples 1 and 2. The sodium alginate is Grade 10/60 available from Protan Ltd.

The water swellable wound dressing film is prepared as follows. First, components A to E are mixed thoroughly to form a first precursor mixture. Components F and G are mixed to form a second precursor mixture. Then the first and second precursor mixtures are mixed thoroughly to form an aqueous gel, which is spread by a knife over a roll coater to produce a film. The film sets within 2 minutes at ambient temperature, which makes this composition especially suitable for a continuous production process. The gel is dried in air at 80° C. for 1 hour. The resulting film is stronger than the film of Example 2.

EXAMPLE 4

A swellable wound dressing film comprising alginate ester and a cationic polymer is prepared from the following constituents (percentages are by weight):

| | | |
|---|---|---|
| A | 2% | Propylene Glycol Alginate (PGA) |
| B | 13% | Propylene Glycol |
| C | 13% | Glycerol |
| D | 2% | Chitosan |
| E | 70% | Water |

I claim:

1. A water swellable wound dressing material comprising, by weight based on the weight of the material when anhydrous:

from 5% to 50% of an alginate ester of a $C_1$–$C_6$ polyhydric alcohol;

from 50% to 95% of a humectant consisting of one or more $C_1$–$C_6$ monohydric or polyhydric alcohols; and from 0% to 30% of water, provided that the wound dressing material comprises less than 1.5% by weight of polyvinyl alcohol.

2. The water swellable wound dressing material of claim 1, wherein the alginate ester comprises propylene glycol alginate.

3. The water swellable wound dressing material of claim 1, wherein the degree of esterification of the alginate ester is from 35% to 95%.

4. The water-swellable wound dressing material of claim 1, wherein the humectant is selected from the group consisting of glycerol and propylene glycol.

5. The water-swellable wound dressing material of claim 1, wherein the material contains from 10% to 25% by weight of the alginate ester.

6. The water-swellable wound dressing material of claim 1, wherein the material contains from 65% to 90% by weight of the humectant.

7. The water-swellable wound dressing material of claim 1, wherein the material contains from 5% to 15% by weight of water.

8. The water-swellable wound dressing material of claim 1 further comprising one or more substances that are pharmacologically active to promote wound healing, and which are present in an amount not exceeding about 25 % by weight.

9. The water-swellable wound dressing material of claim 8 wherein the said one or more substances that are pharmacologically active to promote wound healing are selected from the group consisting of cytokines and biopolymers other than an alginate.

10. The water-swellable wound dressing material of claim 1, and further comprising an antimicrobial substance, in an amount not exceeding about 2% by weight.

11. The water swellable wound dressing material of claim 1, wherein the alginate ester is ionically cross-linked by polyvalent cations.

12. The water swellable wound dressing material of claim 11, wherein the polyvalent cations are selected from the group consisting of calcium cations and zinc cations.

13. The water swellable wound dressing material of claim 1, wherein the alginate ester is covalently cross-linked.

14. The water swellable wound dressing material of claim 1, wherein the material further comprises from 5% to 20% by weight based on the weight of the material when anhydrous of a substantially non-esterified alginate.

15. The water swellable wound dressing material of claim 1, wherein the material further comprises from 10% to 35% by weight based on the weight of the material when anhydrous of gelatin or a water swellable polysaccharide other than an alginate.

16. The water swellable wound dressing material of claim 15, wherein the water swellable polysaccharide is selected from the group consisting of gellan gum, agar, a cellulose derivative and a starch derivative.

17. The water swellable wound dressing material of claim 1, wherein the material further comprises from 5% to 20% by weight based on the weight of the material when anhydrous of a cationic polymer.

18. The water swellable wound dressing material of claim 17, wherein the cationic polymer comprises cationic chitosan.

19. The water swellable wound dressing material of claim 1 in the form of a continuous or perforated film.

* * * * *